United States Patent [19]

Racz et al.

[11] 4,217,499

[45] Aug. 12, 1980

[54] TOMOGRAPHIC SCANNING APPARATUS WITH IONIZATION DETECTOR MEANS

[75] Inventors: Janos A. Racz, San Jose; Edward J. Seppi, Menlo Park, both of Calif.

[73] Assignee: General Electric Company, Milwaukee, Wis.

[21] Appl. No.: 936,150

[22] Filed: Aug. 23, 1978

Related U.S. Application Data

[63] Continuation of Ser. No. 722,931, Sep. 13, 1976, abandoned.

[51] Int. Cl.$^2$ ............................................. G01N 21/34
[52] U.S. Cl. .................................. 250/445 T; 250/385
[58] Field of Search .................... 250/445 T, 374, 385

[56] References Cited

U.S. PATENT DOCUMENTS

| | | |
|---|---|---|
| 3,614,437 | 10/1971 | Allemand et al. |
| 3,930,162 | 12/1975 | Reiss . |
| 3,934,142 | 1/1976 | Hounsfield ...................... 250/445 T |
| 3,991,312 | 11/1976 | Whetten et al. ................. 250/445 T |
| 4,031,396 | 6/1977 | Whetten et al. . |
| 4,047,039 | 9/1977 | Houston . |
| 4,047,040 | 9/1977 | Houston . |
| 4,047,041 | 9/1977 | Houston . |
| 4,051,379 | 9/1977 | Zacher . |
| 4,075,491 | 2/1978 | Boyd .............................. 250/445 T |

*Primary Examiner*—David C. Nelms
*Attorney, Agent, or Firm*—Dana F. Bigelow; Douglas E. Stoner

[57] ABSTRACT

An axial tomography system is disclosed which includes an assembly rotatable about an axis extending along a central opening defined therein, and means for positioning the body portion to be examined within the central opening so that the axis of assembly rotation is perpendicular to a plane passing through the bodily structures to be examined. A source of penetrating radiation is mounted on the assembly toward one side thereof and provides radiation in the form of a fan beam. Means are provided for rotating the assembly so that the fan beam impinges upon said body portion at a plurality of incident directions. Detector means for the radiation are positioned on the assembly opposite the source, enabling detection of radiation which traverses laterally and is not absorbed in the thin body section in which the aforementioned plane resides. The detector means is preferably of the ionization type, and may comprise an array of side-by-side mutually insulated strip electrodes, spaced from a common high voltage electrode. The principal axis of each electrode is oriented along a radius extending toward the radiation source, and the ionization space between such strip and the common electrode can be regarded as defining a cell the principal axis of which is similarly oriented. Collimating means overlie the detector means and serve to assure that the radiation incident on each such cell is only that which has passed through an appropriate element of the body portion being examined.

5 Claims, 6 Drawing Figures

TO CONTROL AND IMAGE RECONSTRUCTION STATION

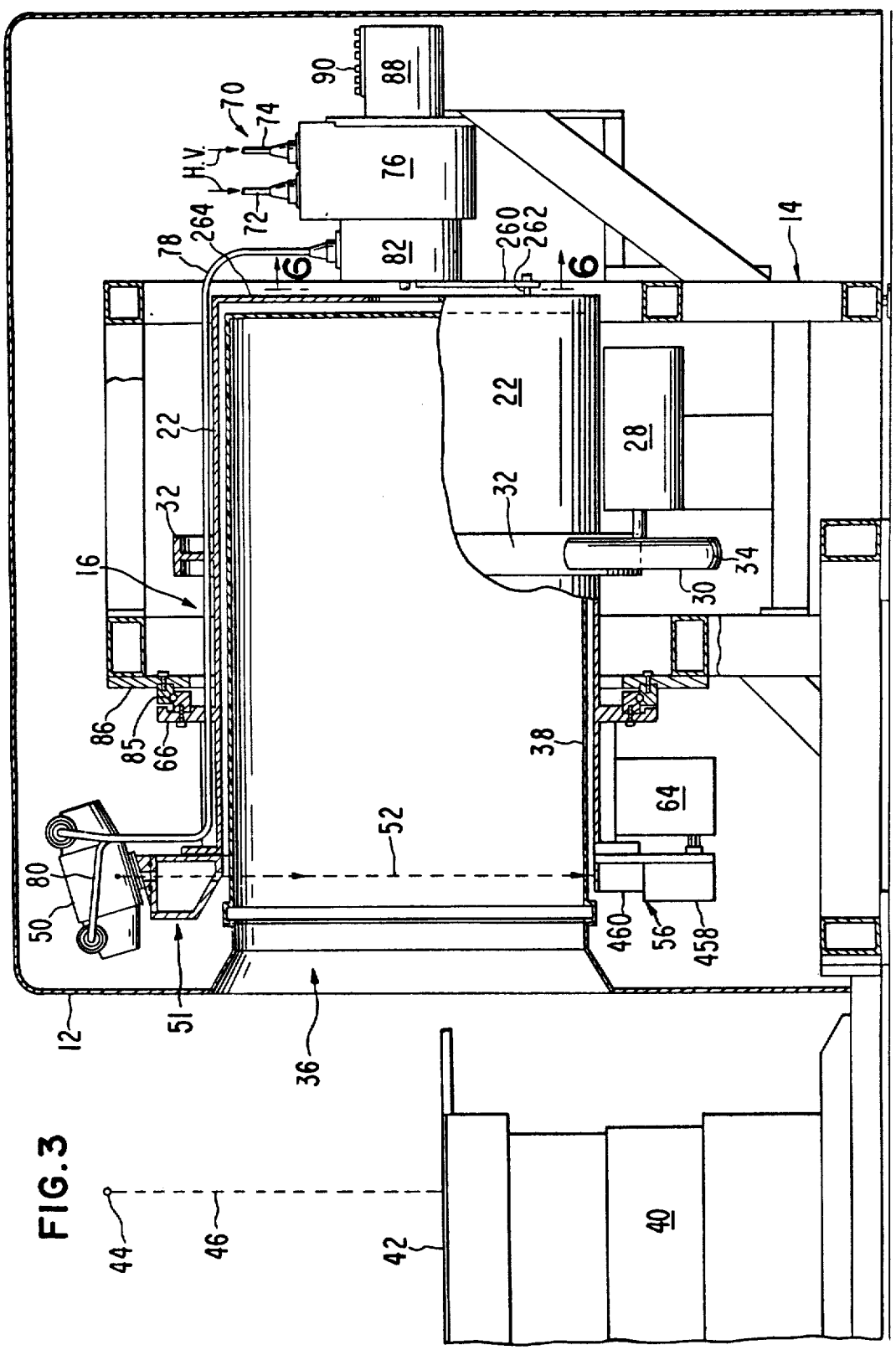

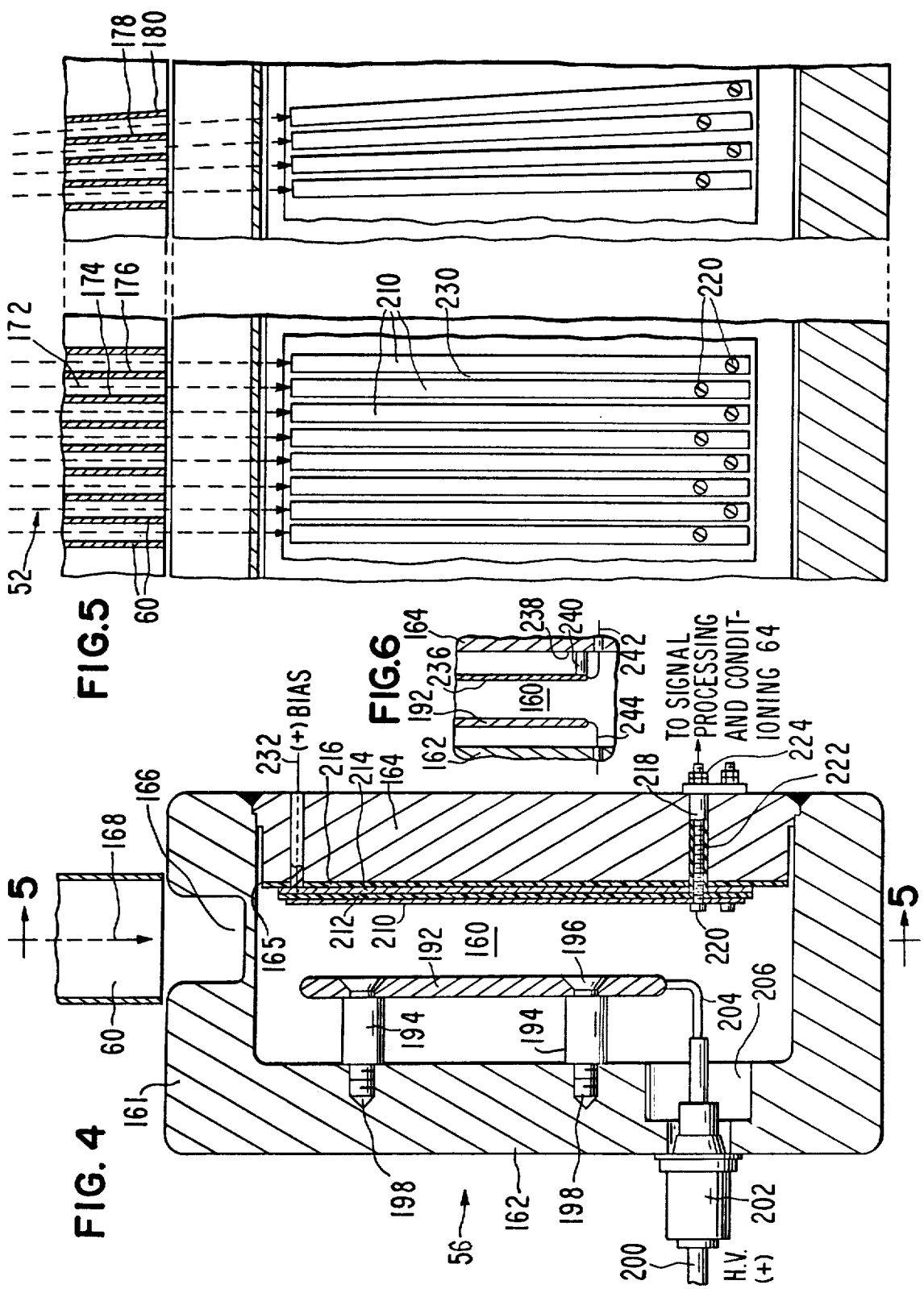

TOMOGRAPHIC SCANNING APPARATUS WITH IONIZATION DETECTOR MEANS

This is a continuation of application Ser. No. 722,931 filed Sept, 13, 1976 now abandoned.

BACKGROUND OF THE INVENTION

This invention relates generally to medical diagnostic apparatus and methodology, and more specifically relates to X-ray scanning apparatus of the type utilized in computerized tomography.

Within very recent years, a relatively enormous degree of interest has been evidenced on the part of medical diagnosticians in a field now widely known as computerized tomography. In a typical procedure utilized in computerized tomography (or CT), an X-ray source and detector means are positioned on opposite sides of the portion of the patient which is to be examined. In the prior art these paired elements are made to transit across the body portion to be examined, while the detectors measure the X-ray absorption at the plurality of transmission paths defined during the transit process. Periodically as well, the paired source and detector means are rotated to a differing angular orientation about the body, and the transit process repeated. A very high number of absorption values may be yielded by procedure of this type, and the relatively massive amounts of data thus accumulated may be processed by a digital computer—which cross-correlates the absorption values to thereby derive absorption values for a very high number of points (typically in the thousands) within the section of the body being scanned. This point by point data may then be combined to enable reconstruction of a matrix (visual or otherwise) which constitutes an accurate depiction of the density function of the bodily section examined. The skilled diagnostician, by considering one or more of such sections, may diagnose various bodily elements such as tumors, blood clots, cysts, hemorrhages and various abnormalities, which heretofore were detectable, if at all, only by much more cumbersome and, in many instances, more hazardous (from the viewpoint of the patient) techniques.

While apparatus of the aforementioned type have therefore represented powerful diagnostic tools, and have been deemed great advances in the radiography art, apparatus heretofore designed and commercially available have suffered from many of the shortcomings incident to first generation devices. Thus, for example, it may be noted that acquisition of the raw data obtained as an incident of the discussed techniques frequently entailed an undesirably long period—which among other things subjected a patient to both inconvenience and stress. The patient's inability to remain rigid for such a lengthy period, also could lead to blurring of the image sought to be obtained.

In a copending application of John M. Pavkovich and Craig S. Nunan, Ser. No. 643,894 filed on Dec. 23, 1975 entitled "Tomographic Apparatus and Method for Reconstructing Planar Slices from Non-absorbed Radiation", and as well in the similarly copending application of John M. Pavkovich entitled "Apparatus and Method for Reconstructing Data", filed on Dec. 23, 1975, under Ser. No. 643,896, both applications of which are assigned to the same assignee as is the present application, apparatus and methodology are disclosed which alleviate a number of the prior art problems, most notably including the lengthy period that has heretofore been involved in computer processing of the raw data provided by the detectors. The apparatus therein disclosed utilizes a fan beam source of radiation coupled with application of a convolution method of data reduction, with no intervening reordering of fan rays, to thereby eliminate the errors and delays in computation time which would otherwise be involved in such reordering. The radiation source and the detector means are positioned on opposite sides of the portion of the patient to be examined and these elements are made to rotate through a revolution or portion thereof while the detectors measure the radiation absorption at the plurality of transmission paths defined during the rotational process.

In tomographic scanning apparatus heretofore widely known in the art, the detectors most commonly utilized for responding to the X-ray source took the form of scintillation counters which in turn were coupled to photomultipliers for providing suitable signal output levels. Detectors of this type, however, are known to suffer from several significant deficiencies. The scintillation crystals, for example, display hysteresis effects, i.e., they retain a memory of their earlier excitation state. Further, the photomultipliers which are utilized as an adjunct of the scintillation crystals, are relatively unstable elements which require frequent maintenance and attention, and are, in addition, relatively expensive.

While ionization detectors are well known as measuring elements for detecting radiation in X-ray or similar systems, it has not heretofore been deemed practical or appropriate to incorporate devices of this type into scanning systems of the type considered herein. This is in view of what has been deemed a necessity for relatively long path lengths in the cell elements comprising such detectors. In general, a problem of that type can presumably be overcome by providing relatively high gas pressures in the detector cells; but heretofore acceptable designs have not been forthcoming.

SUMMARY OF INVENTION

Now in accordance with the present invention, scanning apparatus is provided which includes an assembly rotatable about an axis extending along a central opening defined therein, and means for positioning the body portion to be examined within a central opening so that the axis of assembly rotation is perpendicular to a thin, generally planar section of the body portion to be scanned. A source of penetrating radiation, as for example of X-rays or gamma rays is mounted on the assembly toward one side thereof, and provides radiation in the form of a fan beam. Means are provided for rotating the assembly so that the fan beam impinges upon the body portion at a plurality of incident directions.

Detector means for the radiation are positioned on the assembly opposite the source, enabling detection of nonabsorbed radiation proceeding laterally across the section. In accordance with the invention, the detector means is preferably of the ionization type, and may comprise an array of side-by-side mutually insulated strip electrodes, spaced for a common high voltage electrode. The principal axis of each electrode is oriented along a radius extending toward the radiation source, and the ionization space between such strip and the common electrode can be regarded as defining a "cell" the principal axis of which is similarly oriented. A suitable atmosphere of a high Z gas such as xenon, a mixture of xenon with a small proportion of krypton is maintained within the cell environment, typically at pressures of the order of about 10 atmospheres or higher. The plurality of such cells are located within a suitable enclosure to maintain the desired pressurization, and electrical feed-throughs pass through the said enclosure and are suitably insulated and sealed to enable application of high potential to plate members of the cells, and also to enable read out of the ionization current signals from other electrode members of the cells.

Collimating means directly overlie the detector means and serve to assure that the radiation incident on the cell defined by each electrode strip is only that which has passed through that element of the body portion being examined, which is intended for detection at the particular cell.

Signal processing and conditioning means for receiving the output signals from the detector means and amplifying and converting such signals to digital form, are also mounted on the rotatable assembly adjacent to the detector and collimator assembly, and are movable with the rotatable assembly. The signals from the detector are therefore provided to the closely adjacent processing and conditioning means, which amplify and convert the signals provided thereto to a suitable form for further processing.

BRIEF DESCRIPTION OF DRAWINGS

The invention is diagrammatically illustrated, by way of example, in the drawings appended hereto in which:

FIG. 3 is a side elevational view of the apparatus of FIGS. 1 and 2 therein, the view being partially broken away and in section;

FIG. 4 is a transverse cross-sectional view of the detector assembly portion of the present apparatus;

FIG. 5 is a partial plan view of the FIG. 4 apparatus, taken along the line 5-5 therein;

FIG. 6 is a partial cross-sectional view similar to FIG. 4, and illustrating a further embodiment of the invention.

DESCRIPTION OF THE PREFERRED EMBODIMENT

Figure 1:
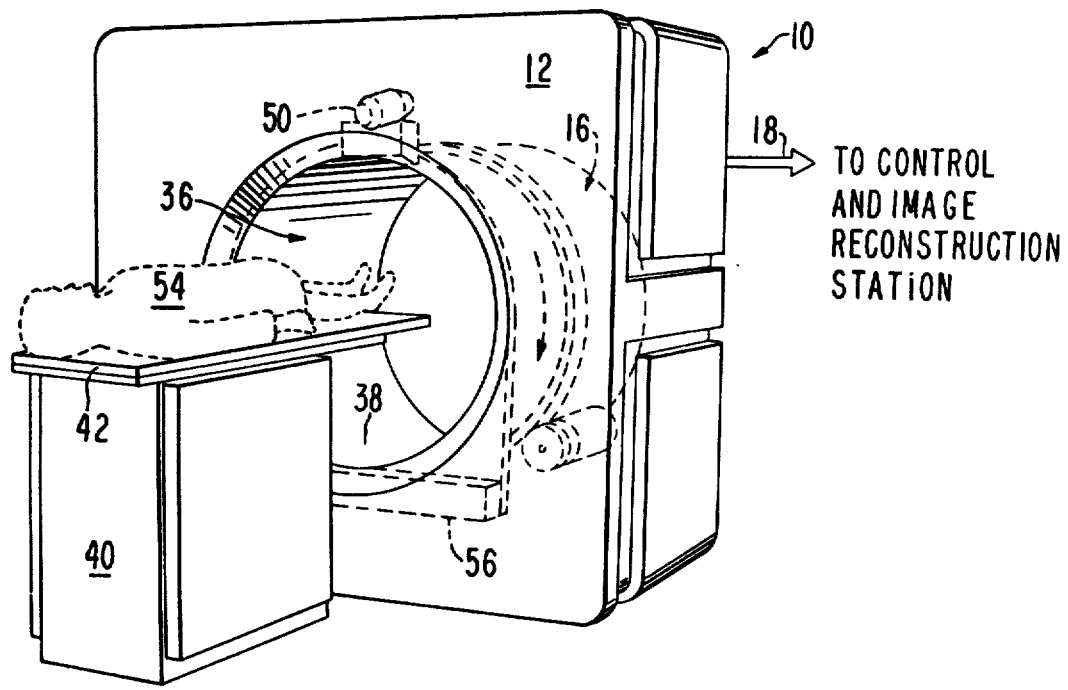
FIG. 1 is an external perspective view, somewhat schematic in nature, of scanning apparatus in accordance with the present invention.

In FIG. 1 herein an external perspective view appears, the view being somewhat simplified in nature, and setting forth scanning apparatus 10 in accordance with the invention. This view may be considered simultaneously with the views of FIGS. 2 and 3. With certain exceptions, importantly including the detector assembly (which will be fully discussed hereinbelow) apparatus 10 is substantially that disclosed in an application filed by Kendall L. Dinwiddie, et al. on Apr. 19, 1976, under Ser. No. 677,958, and entitled "Tomographic Scanning Apparatus", which application is assigned to the same assignee as is the instant application.

Figure 2:
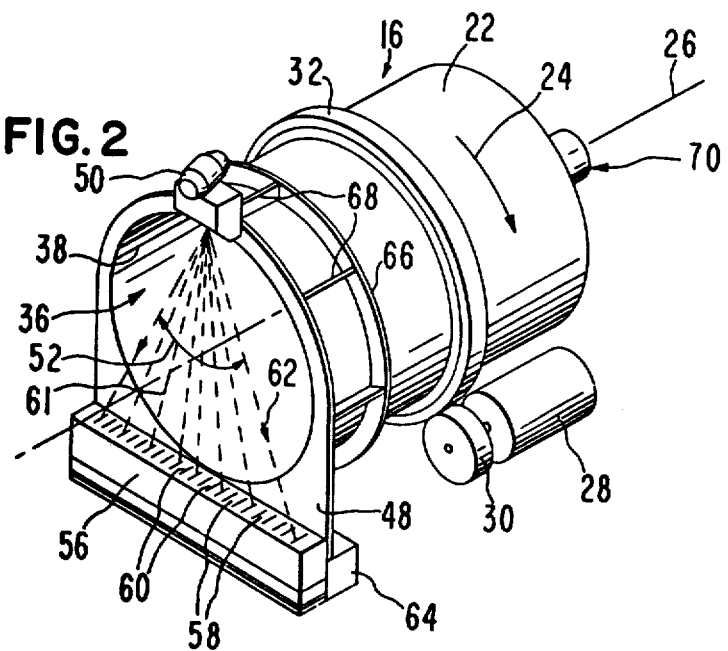
FIG. 2 is a perspective view, again somewhat schematic in nature, depicting the rotatable assembly portion of the FIG. 1 apparatus.

Apparatus 10 is seen to comprise generally an external casing 12 within which a frame 14 (FIG. 3) supports a rotatable assembly 16, which assembly is better seen in FIG. 2. Scanning apparatus 10 forms part of a computerized tomography system, the remaining elements of which principally include control, image reconstruction elements, and image display elements, most of which are contained at a control and image reconstruction station—the details of which are not pertinent to the present invention. Apparatus 10 is in communication with the said station via various control lines, as schematically indicated at link 18 in FIG. 1, which is to say that digital information obtained in consequence of the scanning operations effected by apparatus 10 are furnished to such station; and the latter, in turn, provides both control information for actuating apparatus 10, as well as the various power and excitation potentials, e.g. for the radiation source, the motor, and other elements which are present in apparatus 10.

Rotatable assembly 16 includes an outer cylinder 22 of stainless steel or other metal, and is adapted to be rotated in direction 24 about its central axis 26, by means of a motor 28, the drive wheel 30 of which bears against a drive collar 32 which is secured about cylinder 22. Wheel 30 may thus include a rubber surface 34 or the like, which by virtue of its high coefficient of friction, is effective in causing non-slip rotation of cylinder 22.

By comparing FIGS. 1 and 2 it will be evident that the central opening 36 of rotatable assembly 16 serves to receive a patient 54 who is to be examined within apparatus 10. A sleeve 38 of plastic or the like is secured to casing 12, and provides a stationary reference frame which has certain advantages—especially psychologically for the patient who is positioned within opening 36.

The patient 54 during use of apparatus 10 is positioned upon the top surface 42 of a positioning bench 40, the surface 42 being movable along axis 26 so as to enable movement of the patient into the apparatus. A laser source 44 is positoned in front of apparatus 10 at an overhead position (FIG. 3) so that the beam 46 thereof impinges upon the patient at an axial location—to aid in proper alignment of the patient during the examination process. The laser may also be affixed to portions of casing 12. The bench 30 may include actuating means which enable incremental advance of same, so as to facilitate successive transverse scan sections through the body of patient 54, and which also enable movement of the bench in other directions to facilitate patient positioning.

The forward end of assembly 16 carries a plate 48, at the periphery of which is mounted a radiation source 50—preferably comprising an X-ray source capable of projecting an X-ray pattern in the form of a fan beam 52. Fan beam 52 may be yielded by a collimator 51 which is positioned in front of the X-ray emission source—as is known in the art. Fan beam 52 is preferably (though not necessarily) at least as wide as the object to be examined, which in the present instance, of course, constitutes patient 54.

A detector means generally indicated at 56 is mounted directly opposite source 50, i.e. toward the opposite edge of plate 48. Although other types of detectors suitable for use with X-rays and similar electromagnetic radiation may be utilized, such as crystal scintillators coupled with photomultipliers or photodiodes or so forth, detector means 58 preferably comprises an array of ionization detectors, i.e. detectors which function by measuring ionization generated in a high Z-gas such as xenon krypton, or xenonkrypton (i.e. xenon with a small proportion of krypton).

As will be more fully appreciated in connection with the showings of FIGS. 4 and 5, a series of collimator plates 60 are provided, the purpose of which is to assume that the current generated by a given "cell" in the plurality of detectors, represents substantially only that induced by radiation proceeding along the radius from such cell to the source 50.

It will be seen that detector means 58 is in very close physical proximity to a signal processing and conditioning means, generally indicated at 64. Indeed, in the apparatus depicted these two blocks are back to back with respect to one another. This close physical proximity has important advantages in the present environment in that the close proximity of these elements—which are commonly rotatable with assembly 16—minimizes the possibility of introducing spurious signals into the various detector channels. This is particularly significant in the present instance in that the high potentials associated with the X-ray source etc. increases the likelihood of introducing such spurious signals.

The assembly 16 in addition to including the several elements thus far described, includes certain strengthening elements such as the reinforcing ring 66 and cross braces 68. The purpose of these several elements is to increase, to the extent practical, the rigidity of the overall assembly 16, thereby decreasing the effects of vibration and the possibility of undesired flexure, all of which can be particularly detrimental with respect to the detector structures—i c., stressing of certain of these structures can change the electrical response characteristics of same, thereby introducing erroneous readings.

In the case of X-ray diagnosis the thickness of fan beam 52 as defined by the collimators is typically between 1 mm and 15 mm at the middle of the object. It will be understood that as the source-detector array undergoes relative rotation with respect to the patient (continuously where exact reconstruction is desired) over a time of approximately 1 to 15 seconds, readings of absorbed radiation are measured by detector means 56. The data acquisition may be completed during one relative revolution (i.e. 360 degrees) of the system; the present system is also well adapted to acquire the data over the course of several revolutions—which can provide superior images because of the increased quantity of data. As further described in the aforementioned copending applications of Pavkovich, et al. Ser. No. 643,894 and Dinwiddie, et al. Ser. No. 677,958, data from detector means 56, after suitable processing and conditioning, is provided to a control and image reconstruction station where it is convolved, appropriately stored and later back-projected with other data to produce an output picture which is a replica of the thin cross-section of patient 54 which has been examined. It will of course be understood that the data need not be necessarily converted into a visually discernable picture; but can be expressed in other analytical forms, i.e. numerically or so forth.

As may be seen by consideration of FIG. 3, electrical interconnections to all portions of assembly 16 which require same, is effected via a slip ring assembly (details not shown) which is generally indicated at 70. In particular, it will be observed that high voltage input lines 72 and 74 are provided to the casing portion 76 of assembly 70, which portion is stationary. The slip ring interconnection provides the required excitation connections to X-ray source 50 via the cables 78 and 80 which proceed from casing portion 82 of assembly 70. The latter, portion 82, rotates with rotating assembly 16, which is supported on bearing 85 between ring 66 and a frame ring 86. In particular, rotation of portion 82 is effected commonly with the cylinder 22 by means of a link 260 which is secured to portion 82 and engages a pin 262 which projects from the rearward side 264 of cylinder 22.

Similarly the various further low votage interconnections, i.e. for the detector outputs, for the various low voltage control signals for the electrical elements mounted on plate 48, and for the low voltage inputs to source 50 (for the anode rotor), are all enabled by means of slip ring connections contained within portion 88 of slip ring assembly 70. Thus several of the external connections 90 appear at portion 88. The external casing of portion 88 is, of course, stationary.

In FIG. 4 herein a transverse cross-sectional view is set forth of the detector 56. This Figure may be considered simultaneously with FIG. 5, which sets forth a partial plan view of the collector electrode structure present in the detector, the view being taken along the direction 5—5 of FIG. 4. Detector 56 is seen to generally comprise a completely enclosed chamber 160 which is defined by a C-shaped member 162 joined with a plate 164, with end portions being provided at each end of the relatively extended chamber 160, as may be seen, e.g. in FIG. 2.

The outwardly facing upper portion 161 of member 162 includes a recessed groove or window 166 which extends for substantially the entire length of portion 161. The member 162, as well as plate 164 typically comprises a material such as aluminum, and the reduced thickness effected by virtue of window 166, permits radiation proceeding, e.g. in the direction of line 168 to enter into chamber 160.

By comparing FIGS. 4 and 5 it will be seen that the radiation of fan beam 52 proceeding toward detector 56 passes initially through the collimator plates 60. These plates have been briefly alluded to in connection with FIG. 2, and the function of the same is to assure that stray radiation is absorbed thereby, so that the radiation proceeding between a pair of collimator plates such as at 174 and 176, is substantially only that proceeding along the radius extending to such source from the collimator plates. Thus the midline 172 between plates 174 and 176 is oriented along such a radius to the X-ray source 50. As will be noted in FIG. 5, the collimator plates 60 are oriented with an increasing inclination from the vertical as one proceeds from the mid-point of the detector array toward the ends thereof, so that collimator plates such as at 178 and 180 are rather substantially inclined as to be aligned with the outermost rays of fan beam 52, as for example, ray 62 in FIG. 2.

In the present construction a single, i.e. a common high voltage electrode 192 is provided within chamber 160. Such element which may, for example, comprise stainless steel or the like, thus extends substantially for the length of chamber 160 (except of course that the lateral ends of electrode 192 terminate short of the spaced end walls of the said chamber, to preclude electrical contact therewith. The electrode 192 is supported from C-shaped member 162 by insulator stand-offs 194, by fasteners 196 which enter the facing ends of the standoffs. These standoffs 194 are in turn secured to member 162, as at 198.

A high voltage positive potential is provided to the common high voltage electrode 192 by means of a cable 200, which passes through a suitable connector 202 mounted in the wall of detector 56, with conductor wire 204 proceeding from cable 200 being in electrical contact with electrode 192. Connector 202 where it is engaged with the opening 206 through the wall of member 162 is provided with suitable gaskets to assure a pressure tight seal. This is necessary, of course, in that a relatively elevated gas pressure is maintained within chamber 60, i.e. by the presence of a high Z gas such as xenon, krypton or a suitable mixture of the two, which gases are typically maintained at a pressure of the order of 10 atmosphere or higher. The potential applied to electrode 192 will typically be of the order of 500 to 5,000 volts.

The collector structure in the present apparatus comprises a plurality of narrow and elongated electrically electrically conductive electrode strips 210. Such strips are present as individual discrete elements on a common insulating backing 212 which may, for example, comprise a plastic such as mylar or similar good insulator. The distinct electrode strips 210 can be thus formed on insulating layer 212 by techniques known in the art, including, e.g. by the use of photoetching methodology. Although the combination of insulating backing member 212 and electrodes 210 can be directly affixed to the adjacent face 165 of plate 164, it is preferable, as shown in FIG. 4, for an intervening thin metallic layer to be provided as at 214, together with a further insulating layer 216, which is in turn directly in contact with the innermost face 165 of plate 164. The advantages of this further arrangement will shortly become evident.

Electrical connection is effected to each of the aforementioned strip electrodes 210 by means of suitable connectors as at 218 which at the end 220 thereof are in electrical contact with the individual strips and are insulated as at 222 in their passage through the intervening structures. The output signal from the detector strip electrode is taken at 224 and provided to signal processing and conditioning means 64. (FIG. 2)

By referring to the partial plan view of FIG. 5 it will be seen that the principal axis of each of the elongated generally rectangular strip electrodes 210 is aligned with the midline through the spacing between an associated overlying pair of collimator plates 60, and the principal axis of the various strip electrodes 210 therefore display increasing inclination from the vertical as one proceeds away from the center of the detector array, as may be seen, e.g., from inspection of the right side of FIG. 5.

It will be evident that in effect each individual strip electrode 210 defines with a portion of the common but spaced high voltage electrode 192, a detector "cell"—which includes the two elements just mentioned, and the intervening ionization space. Effectively, therefore, the present arrangement provides a plurality or array of such detection cells, i.e. one such discrete "cell" for each of the strip electrodes 210. Thus in a representative device in accordance with the invention, 301 such strip electrodes may be provided, to thereby establish a totality of 301 such detector cells where each cell can be regarded as elongated, with its principal axis being in the direction of elongation, and oriented along a radius to the radiation source 50. The output signal from each such cell is provided to a separate amplification, processing and conditioning channel within signal processing and conditioning means 64.

It has previously been mentioned that the strip electrodes 210 together with the underlying insulating layer 214, can be directly secured (e.g. by heat lamination, use of adhesives or so forth) to the conductive innerface 165 of plate 164. With this arrangement, however, difficulties can arise in that charge produced in the inter-electrode gaps between high voltage plates 192 and the electrode strips 210, can impinge upon the insulated spaces as, e.g. at 230, between adjacent strip electrodes 210. This in turn can lead to erroneous signal readings. In the embodiment of FIG. 4 this problem is overcome by use of the additional conductive layer 214, which may be provided with a small positive bias as at 232. This bias may be of the order of a couple to several hundred volts, and serves to repel any space charge tending to settle in areas such as 230.

The problem dealt with by the foregoing construction, i.e. the settling of charge upon the areas 230 between strip electrodes, can be effectively overcome by another construction, as shown in the embodiment of FIG. 6. In this embodiment, the high voltage electrode 192 is identical to that depicted in FIG. 4. Thus electrode 192 is again common to the array of detection cells defined with the plurality of strip electrodes. In the present embodiment, however, the strip electrodes 236, instead of residing upon a backing surface of an insulator, are discrete metallic strips, which are spaced from the inner wall 238 of plate 164 by means of insulator standoffs 240. Only one such standoff is shown in the highly simplified view of FIG. 6; in practice two or more may be provided in order to enable accurate electrode spacing and sufficient rigidity. The connections in FIG. 6, both to the individual collector electrodes as at 242, and to the high voltage plate 192 as at 244, are shown in schematic fashion. It will be appreciated that as in the embodiment of FIG. 4, these connections pass through the walls of the detector assembly in such fashion as to be electrically insulated therefrom, and also in the presence of suitable gasketing or other sealing means, to assure that the positive gas pressure is adequately maintained within the ionization chamber 160.

While the present invention has been set forth in terms of specific embodiments thereof, it will be understood in view of the instant disclosure that numerous variations upon the invention are now enabled to those skilled in the art, which variations yet reside within the scope of the present teachings. Accordingly the invention is to be broadly construed and limited only by the scope and experience of the claims now appended hereto.

We claim:

1. In a computerized tomographic system for examining a subject by means of penetrating radiation to enable reconstruction of a representation of the structure residing in a section taken through said subject; said system comprising:

source means for causing penetrating radiation in the form of a substantially planar sheet to enter said subject at a plurality of locations around said section, and detector means for detecting radiation passing through said section; and signal processing means for receiving the output signals from said detector means;

the improvement wherein:

said detector means comprises a sealed chamber containing gas which is ionizable by said radiation, an elongated window in one wall of said chamber for admitting said radiation, said window lying in the plane of said radiation sheet, said chamber having two side walls extending from said window wall in a direction away from said source, a substantially planar electrode in said chamber adjacent one of said side walls, a plurality of elongated detector electrodes supported in said chamber on one side of an insulating sheet means which is supported by the other of said side walls, said detector electrodes being spaced apart from each other and facing said planar electrode, said detector electrodes having their long dimension extending toward said window wall, the surface of said planar electrode which faces said detector electrodes lying in a plane substantially parallel to the long axis of said elongated window, and electrical leads separately connecting each of said detector electrodes to said signal processing means.

2. Apparatus in accordance with claim 1, wherein said insulating sheet means comprises a first insulating sheet on which said detector electrodes are positioned, an electrically conductive sheet contacting the side of said first insulating sheet non-adjacent said detector electrodes, and a second insulating sheet between said conductive sheet and said other side wall, and said apparatus further comprising means for applying a biasing potential to said conductive sheet for repelling charge from the spaces on said first insulating sheet between said detector electrodes.

3. In a computerized tomographic system for examining a subject by means of penetrating radiation to enable reconstruction of a representation of the structure residing in a section taken through said subject; said system comprising:
source means for causing penetrating radiation in the form of a substantially planar sheet to enter said subject at a plurality of locations around said section, and detector means for detecting radiation passing through said section; and
signal processing means for receiving the output signals from said detector means;
the improvement wherein:
said detector means comprises wall means forming a sealed chamber containing gas which is ionizable by said radiation, means forming a window in said wall means for admitting said radiation into said chamber, a plurality of first electrodes in said chamber and facing second electrode means, said first electrodes being positioned on an insulating sheet with said plural first electrodes being spaced apart from each other on the side of said insulating sheet facing toward said second electrode means, an electrically conductive sheet on the side of said insulating sheet opposite from said first electrodes, electrical leads separately connecting each of said first electrodes to said signal processing means, and electrical connection means for applying a biasing potential to said conductive sheet for repelling charges from the spaces on said insulating sheet between said plural first electrodes.

4. Apparatus in accordance with claim 3 wherein said electrically conductive sheet is mounted on a second insulating sheet, and said second insulating sheet is mounted on the inside surface of one wall of said chamber.

5. Apparatus in accordance with claim 4 wherein said second electrode means is electrically insulated from the walls of said chamber.